(12) United States Patent
Jones, Jr.

(10) Patent No.: US 7,531,188 B2
(45) Date of Patent: May 12, 2009

(54) PEST-COMBATING COMPOSITIONS COMPRISING SOY METHYL ESTER

(75) Inventor: Allen L. Jones, Jr., Clayton, NC (US)

(73) Assignee: SMG Brands, Inc., Wilmington, DE (US)

( * ) Notice: Subject to any disclaimer, the term of this patent is extended or adjusted under 35 U.S.C. 154(b) by 49 days.

(21) Appl. No.: 11/117,271

(22) Filed: Apr. 28, 2005

(65) Prior Publication Data

US 2006/0127434 A1    Jun. 15, 2006

Related U.S. Application Data

(60) Provisional application No. 60/635,840, filed on Dec. 14, 2004.

(51) Int. Cl.
  *A01N 25/32* (2006.01)
(52) U.S. Cl. ............... 424/406; 424/405; 514/549; 514/675
(58) Field of Classification Search ............. None
  See application file for complete search history.

(56) References Cited

U.S. PATENT DOCUMENTS

| | | | |
|---|---|---|---|
| 2,283,471 A | 5/1942 | Swaine | |
| 4,975,110 A | 12/1990 | Puritch et al. | |
| 5,035,741 A | 7/1991 | Puritch et al. | |
| 5,098,467 A | 3/1992 | Puritch et al. | |
| 5,098,468 A | 3/1992 | Puritch et al. | |
| 5,106,410 A | 4/1992 | Puritch et al. | |
| 5,389,113 A | 2/1995 | Demmering | |
| 5,424,467 A | 6/1995 | Bam | |
| 5,525,126 A | 6/1996 | Basu | |
| 5,573,700 A * | 11/1996 | Steltenkamp et al. | 510/383 |
| 5,578,090 A | 11/1996 | Bradin | |
| 5,589,181 A | 12/1996 | Bencsits | |
| 5,594,029 A | 1/1997 | Bencits | |
| 5,683,961 A | 11/1997 | Caulder et al. | |
| 5,713,965 A | 2/1998 | Foglia | |
| 6,001,874 A * | 12/1999 | Veierov | 514/533 |
| 6,015,440 A | 1/2000 | Noureddini | |
| 6,034,034 A | 3/2000 | Caulder et al. | |
| 6,174,501 B1 | 1/2001 | Noureddini | |
| 6,203,585 B1 | 3/2001 | Majerczak | |
| 6,218,336 B1 | 4/2001 | Coleman | |
| 6,235,104 B1 | 5/2001 | Barry | |
| 6,281,189 B1 * | 8/2001 | Heimann et al. | 510/491 |
| 6,306,415 B1 | 10/2001 | Reifenrath | |
| 6,398,707 B1 | 6/2002 | Wu | |
| 6,399,800 B1 | 6/2002 | Haas | |
| 6,437,001 B1 | 8/2002 | Roe | |
| 6,444,216 B2 | 9/2002 | Reifenrath | |
| 6,624,124 B2 * | 9/2003 | Garmier | 508/491 |
| 6,797,673 B1 * | 9/2004 | Worthley et al. | 504/148 |
| 6,800,662 B2 | 10/2004 | Roe | |
| 6,930,075 B1 | 8/2005 | Mason | |
| 6,953,814 B2 | 10/2005 | Reifenrath | |
| 7,288,573 B2 | 10/2007 | Roe | |
| 2003/0194454 A1 | 10/2003 | Bessette et al. | |
| 2004/0029974 A1 | 2/2004 | Brandt et al. | |
| 2006/0004130 A1 * | 1/2006 | Strominger et al. | 524/318 |
| 2006/0127434 A1 | 6/2006 | Jones | |
| 2007/0093392 A1 | 4/2007 | Vavra et al. | |
| 2008/0069785 A1 | 3/2008 | Jones | |

OTHER PUBLICATIONS

Proctor & Gamble Chemicals, Material Safety Data Sheet for CE-1618, CE-1618 Kosher, CE-1618LG, Jul. 21, 2004.
Tomah Products, Inc., Material Safety Data Sheet for TOMADOL 1-5, Apr. 29, 2005.
Schuchardt, et al., "Transesterification of Vegetable Oils: A Review" J. Braz. Chem. Soc., 1998, vol. 9, No. 1, 199-210, Brazil.
Fuel Fact Sheets "Biodiesel Production" National Biodiesel Board, http://www.biodiesel.org/pdf_files/fuelfactsheets/Production.PDF, visited website Jul. 27, 2005.
Korus, et al., "Transesterification Process to Manufacture Ethyl Ester of Rape Oil" Proceedings of the First Biomass Conference of the Americas: Energy, Environment, Agriculture,and Industry, 1993, pp. 815-826, vol. II. National Renewable Energy Laboratory, Golden, CO.

* cited by examiner

*Primary Examiner*—Neil Levy
(74) *Attorney, Agent, or Firm*—Hunton & Williams LLP

(57) ABSTRACT

A pest-combating composition including soy methyl ester, and methods of combating pests utilizing same. Such composition in a preferred formulation may also include 2-undecanone. The composition may be constituted as a spray composition, lotion, paste, or other compositional form. Pests that may be usefully combated with such composition include mosquitoes, ticks, cockroaches, thrips, deer fly, gnats, and aphids.

19 Claims, No Drawings

PEST-COMBATING COMPOSITIONS COMPRISING SOY METHYL ESTER

CROSS-REFERENCE TO RELATED APPLICATION

The benefit of U.S. provisional patent application No. 60/635,840 filed Dec. 14, 2004 in the name of Allen L. Jones, Jr. for "Increasing Effectiveness of Insect Repellent and Pest Control Actives by Volatility Modification," is hereby claimed.

FIELD OF THE INVENTION

The present invention relates to compositions having utility for combating pests, including mosquitoes, ticks, and other arthropods and insect species.

DESCRIPTION OF THE RELATED ART

In the field of insecticides and pesticides, as well as insect and pest repellents, much effort has been given to the development of compositions that are "environmentally friendly." Accordingly, there has been a great interest in compositions that are readily biodegradable or otherwise compatible with human and animal use as formulations having little or no toxicity.

Pest species include mosquitoes, ticks, flies and other insect species that are vectors of human disease-causing agents. Mosquitoes and ticks are of primary interest as disease carriers. Mosquitoes and ticks, for example, carry Lyme disease, encephalitis, and other diseases. Mosquitoes and ticks transmit the widest variety of pathogens out of all blood-sucking arthropods. As a result, there has been great interest in developing an insect repellent that is efficacious for control of mosquitoes and ticks, and which is more effective than repellents based on N,N-diethyl-m-toluamide (DEET).

Although there has been increasing use of various natural ingredients in pest-combating compositions, such natural ingredients typically are utilized in the form of isolates or purified species, rather than being chemically processed to other ingredient forms. This self-imposed limitation on the formulation of so-called "green" products has in many cases limited the chemical efficacy of the compositions for their intended pest-combating usage.

In consequence, the art continues to seek improvements in natural product formulations for combating insects and other pests.

SUMMARY OF THE INVENTION

The present invention relates to pest-combating compositions containing as an active ingredient, soy methyl ester.

In one aspect, the invention relates to a composition of such type, further including 2-undecanone.

In another aspect, the invention relates to a DEET-free pest-combating composition including soy methyl ester.

In a further aspect, the invention relates to a composition of a foregoing type, formulated as a spray, lotion or sunblock composition.

A further aspect of the invention relates to an article or region, to which has been applied a pest-combating composition comprising soy methyl ester.

Another aspect of the invention relates to a packaged insect repellent, comprising a container holding an insect repellent composition including soy methyl ester.

A still further aspect of the invention relates to a method of combating pests, at a locus containing or susceptible to the presence of same, such method including applying to at least a portion of such locus a pest repellent composition including soy methyl ester.

Other aspects, features and embodiments of the invention will be more fully apparent from the ensuing disclosure and appended claims.

DETAILED DESCRIPTION OF THE INVENTION, AND PREFERRED EMBODIMENTS THEREOF

The disclosure of U.S. provisional patent application 60/635,840 filed Dec. 14, 2004 in the name of Allen L. Jones, Jr. for "Increasing the Effectiveness of Insect Repellent and Pest Control Actives by Volatility Modification," is hereby incorporated herein by reference, in its entirety.

The present invention is based on the discovery that soy methyl esters are unexpectedly and highly effective as pest-combating active ingredients in the pest control formulations. As used herein, the term "soy methyl ester" refers to methyl ester(s) of fatty acids or oleochemicals of soybean oil, and sometimes is referred to as soybean oil methyl ester or as soybean methyl ester. Soy methyl esters are readily produced by subjecting fatty acids and oleochemicals of soybean oil to transesterification chemical reaction, e.g., a base-catalyzed transesterification of soybean oil. Soy methyl esters of widely varying types are usefully employed in the practice of the invention. One particularly preferred soy methyl ester comprises a mixture of $C_{16}$-$C_{18}$ saturated and $C_{18}$ unsaturated methyl esters, identified by Chemical Abstracts Registry Number (CAS#) 67762-38-3.

Soy methyl esters usefully employed in compositions of the present invention are readily commercially available, e.g., under the brand name "Enviro-Saver" from Columbus Foods Company (Chicago, Ill.), under the brand name "Ecoline Soya Methyl Esters" from Cortec Corporation (St. Paul, Minn.), and otherwise as fatty acid methyl ester from Cargill Industrial Oils & Lubricants (Minneapolis, Minn.), as methyl soyate from Cognis Corporation (Cincinnati, Ohio), and as soy methyl esters from Vertec BioSolvents, Inc. (Downers Grove, Ill.), Lambent Technologies Corporation (Gurnee, Ill.), soy-based fatty acid esters from Chemol Company, Inc. (Greensboro, N.C.), SoyGold 1000 from Ag Environmental Products (Omaha, Nebr.), and Steposol SB-D and Stepasol SB-W soy methyl esters from Stepan Company (Northfield, Ill.).

In formulating the soy methyl ester in useful formulations for combating pests such as mosquitoes and ticks, the soy methyl ester is advantageously formulated as an emulsified base to which are added carrier, adjuvant and other ingredients of the composition. For example, the additional ingredients may include fillers, dispersants, water or other solvent medium or media, surfactants, suspension agents, sticking agents, stabilizers, preservatives, dyes, pigments, masking agents, emollients, excipients, post-application detection agents, and additional active ingredients. Such additional active ingredients may include, for example, additional pest-combating ingredients, such as repellents or cidal agents. By way of example, the soy methyl ester emulsion may be formulated with an insect repellent ingredient such as 2-undecanone. As another example, the soy methyl ester emulsion may be formulated with a sunscreen formulation.

A particularly advantageous composition in accordance with the present invention includes soy methyl ester in combination with 2-undecanone. Such composition has been found to provide superior repellency against mosquitoes and ticks. Due to the volatility of 2-undecanone, it is desirable to formulate the composition containing such ingredient with a sticking agent, so that the 2-undecanone in the composition persists at the point of application, to extend the duration of active repellency of the composition. Compositions containing 2-undecanone, in addition to mosquitoes and ticks, exhibit repellency against cockroaches, thrips, deer fly, gnats, aphids, and the like.

Compositions in accordance with the present invention may be formulated in any suitable manner appropriate to the ingredients involved. The soy methyl ester preferably is utilized as an emulsified base for the composition.

The soy methyl ester can be used at any suitable concentration in the compositions of the invention. Preferably, the soy methyl ester has a concentration in the composition of from about 2% to about 15% by weight, based on the total weight of the composition. More preferably, the soy methyl ester has a composition concentration in a range of from about 2.4% to about 12% by weight, based on total weight of the composition. Most preferably, the soy methyl ester has a concentration in the composition in a range of from about 3 to about 10% by weight, based on total weight of the composition.

In one embodiment of the invention, the composition is formulated as a spray composition for administration to the skin of a user. Such composition may contain 2% by weight of soy methyl ester, in a carrier base including, as inert ingredients, purified water, coconut oil, glycerin, geranium oil, citric acid, lecithin, sodium bicarbonate and vanilla.

In another embodiment of the invention, the composition is formulated as a lotion composition for administration to the skin of user. Such composition may also contain, as inert ingredients, purified water, coconut oil, glycerin, geranium oil, citric acid, lecithin, sodium bicarbonate and vanilla.

In yet another embodiment of the invention, the composition is formulated as a spray composition for administration to skin or fur of pets. Such composition may contain 2% by weight of soy methyl ester, purified water, coconut oil, glycerin, geranium oil, castor oil, lecithin and vanilla.

Other compositions of the invention may be formulated as sunblock compositions, containing, in addition to soy methyl ester, zinc oxide, titanium dioxide, and/or small amounts of other sunscreen agents, as well as ingredients such as coconut oil, purified water, glycerin, geranium oil, citric acid, lecithin, sodium bicarbonate, and vanilla.

In addition to compositions of the invention that are formulated for application to body surfaces of users, compositions may be formulated for application or administration to any locus in which it is desired to repel pests against which the compositions of the invention are repellently effective. Such loci may contain or include apparel, furniture, personal accessories, plastic products, cloth products, camping equipment, automotive and vehicular interiors, and the like. For indoor or outdoor usage, the compositions of the invention may be formulated for broadcasting by misting systems or other distribution equipment.

The advantages and features of the invention are further illustrated with reference to the following examples, which are not to be construed as in any way limiting the scope of the invention but rather as illustrative of embodiments of the invention in specific applications thereof.

EXAMPLE I

In this example, various compositions were formulated for comparative testing. The test compositions included: a 1.6% soybean methyl ester emulsion formulated with a commercial sunscreen (Composition A); a 2.4% soybean methyl ester emulsion formulated with a commercial tropical oil (Composition B); a 2.4% soybean methyl ester emulsion formulated with a commercial sunscreen formulation providing an SPF factor of 20 (Composition C); a 4% soybean methyl ester emulsion formulated with 8% undecanone, in a water-based composition (Composition D); and an 8% soybean methyl ester emulsion formulated with 30% undecanone (Composition E). All concentrations are by weight, based on the total weight of the composition. The various compositions A-E were tested for mosquito repellency see as well as tick repellency.

The results are set out in Table 1 below.

TABLE 1

| Composition A | Composition B | Composition C | Composition D | Composition E |
|---|---|---|---|---|
| 1.6% Soybean Methyl Ester emulsion | 2.4% Soybean Methyl Ester emulsion | 2.4% Soybean Methyl Ester emulsion with SPF 20 | 4% Soybean Methyl Ester emulsion with 8% Undecanone | 8% Soybean Methyl Ester emulsion with 30% Undecanone |
| Mosquito: <2 hr | Mosquito: >4 hr | Mosquito: >4.5 hr | Mosquito: >4.5 hr | Mosquito: Not tested |
| Ticks: Not tested | Ticks: <10 min | Ticks: Not Tested | Ticks: >2 hours | Ticks: >2 hours |

The data in Table 1 show that the compositions containing 2.4% and higher concentrations of soy methyl ester demonstrated superior mosquito repellency, and that compositions containing at least 4% soy methyl ester in combination with 2-undecanone demonstrated superior tick repellency, with Composition E yielding performance generally equivalent to that of a permethrin formulation.

EXAMPLE 2

In this comparative test, a composition containing 8% soy methyl ester emulsion with 30% undecanone, the same composition as tested in Example 1 (Composition E), was evaluated for tick repellency, against an untreated control. A 0.5% permethrin composition also was assessed for tick repellency, against an untreated control.

All tests were carried out on paper media, to which native ticks (American dog ticks) were introduced.

The test arena was a 10 cm diameter plastic petri plate (78.5 $cm^2$ bottom surface area). The inside bottom surface was covered with two half circles of white copy paper, separated by a 3 mm void at the centerline. An amount of 537 μL of Composition E sample was applied to the left half of the arena. Ticks, which were unfed males/females of the American dog tick, *Dermacenter vartiabilis*, were added to the arena less than five minutes after treatment with Composition E. The assay was conducted in a dimly lit room, at room temperature. One tick on the treated side was judged to be intoxicated at the two-hour reading.

The results of the test are shown in Table 2 below.

TABLE 2

| Time | Treated (L) | Untreated (R) |
|---|---|---|
| Immediate | 2 | 3 |
| 30 min | 1 | 4 |
| 45 | 2 | 3 |
| 60 | 3 | 2 |

TABLE 2-continued

| Time | Treated (L) | Untreated (R) |
|---|---|---|
| 1 h: 30 min | 1 | 4 |
| 2 h: 00 min | 1 | 4 |

As shown by the foregoing data, the number of ticks on the treated half circle generally remained smaller than the number of ticks on the untreated half circle, throughout the period of the test. Further, the data show that Composition E maintained its tick repellent character over the two-hour period of the test.

EXAMPLE 3

A corresponding test to that of Example 2 was carried out for a 0.5% permethrin composition. It appeared that the ticks were dead at the 60 minute and 2 hour readings. The test data are shown in Table 3 below.

TABLE 3

| Time | Treated (L) | Untreated (R) |
|---|---|---|
| Immediate | 3 | 2 |
| 30 min | 4 | 1 |
| 45 | 4 | 1 |
| 60 | 4 | 1 |
| 1 h: 30 min | 3 | 2 |
| 2 h: 00 min | 3 | 2 |

Comparison of the data in Table 2 and Table 3 showed that Composition E was more effective than the 0.5% permethrin composition throughout the time-frame of the respective tests.

EXAMPLE 4

In this test, the tick repellency of a composition containing 2.4% soybean methyl ester emulsion, Composition B of Example 1, and the composition containing 4% soybean methyl ester emulsion with 8% undecanone, Composition D of Example 1, were assessed.

In the test of Composition B, as evaluated against an untreated control, the test arena was 4 cm in diameter (12.56 cm²) on the back of the left hand of the human male subject. As a control, the left and right halves of the arena were untreated.

To evaluate Composition B, 100 μL of such repellent were applied to the right half of the arena. Ticks, unfed males of the American dog tick, *Dermacenter variabilis*, were added to the arena three minutes after treatment with Composition B.

The times listed in Table 4 below represent minutes after the application of ticks.

The test apparatus was a petri plate top with the opening covered with aluminum screening.

The assay was conducted in light, at room temperature, with the control being conducted first.

The data generated in this evaluation are set out in Table 4 below.

TABLE 4

| | Control | | Composition B | |
|---|---|---|---|---|
| Time | L | R | Untreated (L) | Treated (R) |
| 1 min | 3 | 2 | 5 | 0 ticks |
| 2 | 3 | 2 | 3 | 2 |
| 3 | 4 | 1 | 5 | 0 |
| 4 | 0 | 5 | 5 | 0 |
| 5 | 0 | 5 | 2 | 3 |
| 6 | 4 | 1 | 4 | 1 |
| 7 | 3 | 2 | 3 | 2 |
| 8 | 1 | 4 | 3 | 2 |
| 9 | 3 | 2 | 4 | 1 |
| 10 | 2 | 3 | 4 | 1 |
| 11 | 2 | 3 | 2 | 3 |
| 12 | 2 | 3 | 3 | 2 |
| 13 | 2 | 3 | 2 | 3 |
| 14 | 1 | 4 | 2 | 3 |
| 15 | 1 | 4 | 2 | 3 |

The data in Table 4 show that Composition B was effective as a tick repellent for a period of approximately 10 minutes.

EXAMPLE 5

A corresponding test to that carried out to generate the data of Table 4 in Example 4 was conducted to assess the efficacy of DEET versus untreated human skin, against the American dog tick. The DEET composition contained 10% DEET in absolute ethanol. The test conditions were the same as those employed for evaluation of Composition B in Example 4. The arena was 4 cm in diameter (12.56 cm²) on the undersurface of the left forearm of the human male subjects. The results are shown in Table 5 below, wherein the time is set out in minutes after the application of ticks.

TABLE 5

| | Control | | 10% DEET | |
|---|---|---|---|---|
| Time | L | R | Untreated (L) | Treated (R) |
| 0 min | 3 | 2 | 2 | 3 ticks |
| 1 | 4 | 1 | 2 | 3 |
| 2 | 4 | 1 | 3 | 2 |
| 3 | 4 | 1 | 4 | 1 |
| 4 | 4 | 1 | 3 | 2 |
| 5 | 4 | 1 | 4 | 1 |
| 6 | 3 | 2 | 3 | 2 |
| 7 | 3 | 2 | — | — |
| 8 | 1 | 4 | 4 | 1 |
| 9 | 3 | 2 | 5 | 0 |
| 10 | 2 | 3 | 5 | 0 |
| 11 | 3 | 2 | 3 | 2 |
| 12 | 3 | 2 | 2 | 3 |
| 13 | 2 | 3 | 4 | 1 |
| 14 | 2 | 3 | 4 | 1 |
| 15 | 2 | 3 | 4 | 1 |

These data illustrate the efficacy of the 10% DEET composition.

EXAMPLE 6

In this example, Composition D was evaluated versus untreated human skin, against the American dog tick. The test arena was 4 cm in diameter (12.56 cm²) on the left inner thigh of the human male subject, just proximal to the kneecap. 100 μL of Composition D were applied to the top half of the arena. Ticks, males of the American dog tick, *Dermacenter variabilis*, were added to the arena two minutes after treatment with Composition D. As a control, the top and bottom halves of the arena were not treated. The test apparatus was a petri plate top with the opening covered with aluminum screening. The assay was conducted in light at room temperature. The control assay was conducted first. The data are set out in Table 6 below, with times in minutes after application of ticks.

TABLE 6

| | Control | | Composition D | |
|---|---|---|---|---|
| Time | T | B | Treated (T) | Untreated (B) |
| 0 min | | | 5 | 0 ticks |
| 1 | 4 | 1 | 2 | 3 |
| 2 | 4 | 1 | 1 | 4 |
| 3 | 4 | 1 | 0 | 5 |
| 4 | 2 | 3 | 0 | 5 |
| 5 | 3 | 2 | 0 | 5 |
| 6 | 3 | 2 | 0 | 5 |
| 7 | 3 | 2 | 0 | 5 |
| 8 | 4 | 1 | 0 | 5 |
| 9 | 4 | 1 | 0 | 5 |
| 10 | 4 | 1 | 0 | 5 |
| 11 | 4 | 1 | 0 | 5 |
| 12 | 4 | 1 | 0 | 5 |
| 13 | 3 | 2 | 0 | 5 |
| 14 | 3 | 2 | 0 | 5 |
| 15 | 3 | 2 | 0 | 5 |
| 30 | | | 0 | 5 |
| 40 | | | 0 | 5 |
| 50 | | | 0 | 5 |
| 60 | | | 0 | 5 |
| 75 | | | 0 | 5 |
| 90 | | | 1 | 4 |
| 92 | | | 0 | 5 |
| 93 | | | 0 | 5 |
| 94 | | | 1 | 5 |
| 95 | | | 0 | 5 |
| 96 | | | 1 | 4 |
| 97 | | | 0 | 5 |
| 98 | | | 0 | 5 |
| 99 | | | 0 | 5 |
| 100 | | | 0 | 5 |
| 105 | | | 0 | 5 |
| 110 | | | 0 | 5 |
| 115 | | | 0 | 5 |
| 120 | | | 0 | 5 |
| 135 | | | 0 | 5 |
| 150 | | | 0 | 5 |

The data shown in Table 6 evidence superior efficacy of Composition D in repelling ticks.

EXAMPLE 7

In this example, Composition D was evaluated versus untreated human skin, against the American dog tick. The test arena was 4 cm in diameter (12.56 cm$^2$) on the left inner high of the human male subject, just proximal to the kneecap. 100 µL of Composition D were applied to the left half of the arena. Ticks, unfed males/females of the American dog tick, *Dermacenter variabilis*, were added to the arena 30 seconds after treatment with Composition D. As a control, the right and left halves of the arena were not treated. The test apparatus was a petri plate top with the opening covered with aluminum screening. The assay was conducted in light at room temperature. The control assay was conducted first. The data are set out in Table 7 below, with times in minutes after application of ticks.

TABLE 7

| | Control | | Composition D | |
|---|---|---|---|---|
| Time | L | R | Treated (L) | Untreated (R) |
| First group of 5 ticks | | | | |
| 1 min | 2 | 3 | 1 | 4 |
| 2 | 5 | 0 | 3 | 2 |
| 3 | 3 | 2 | 2 | 3 |
| 4 | 5 | 0 | 3 | 2 |
| 5 | 5 | 0 | 2 | 3 |
| 6 | 4 | 1 | 3 | 2 |
| 7 | 4 | 1 | 1 | 4 |
| 8 | 3 | 2 | 0 | 5 |
| 9 | 3 | 2 | 0 | 5 |
| 10 | 4 | 1 | 0 | 5 |
| 11 | | | 3 | 2 |
| 12 | | | 2 | 3 |
| 13 | | | 0 | 5 |
| 14 | | | 2 | 3 |
| 15 | | | 2 | 3 |
| 16 | | | 0 | 5 |
| 17 | | | 0 | 5 |
| 18 | | | 0 | 5 |
| 19 | | | 2 | 3 |
| 20 | | | 1 | 4 |
| 21 | | | 0 | 5 |
| 22 | | | 0 | 5 |
| 23 | | | 0 | 5 |
| 24 | | | 1 | 4 |
| 25 | | | 1 | 4 |
| 26 | | | 2 | 3 |
| 27 | | | 0 | 5 |
| 28 | | | 0 | 5 |
| 29 | | | 0 | 5 |
| 30 | | | 0 | 5 |
| Second group of 5 ticks | | | | |
| 31 | | | 3 | 2 |
| 32 | | | 2 | 3 |
| 33 | | | 3 | 2 |
| 34 | | | 1 | 4 |
| 35 | | | 0 | 5 |
| 36 | | | 1 | 4 |
| 37 | | | 2 | 3 |
| 38 | | | 0 | 5 |
| 39 | | | 2 | 3 |
| 40 | | | 2 | 3 |
| 41 | | | 1 | 4 |
| 42 | | | 1 | 4 |
| 43 | | | 3 | 2 |
| 44 | | | 3 | 2 |
| 45 | | | 2 | 3 |
| 46 | | | 1 | 4 |
| 47 | | | 2 | 3 |
| 48 | | | 2 | 3 |
| 49 | | | 1 | 4 |
| 50 | | | 1 | 4 |
| 51 | | | 1 | 4 |
| 52 | | | 1 | 4 |
| 53 | | | 4 | 1 |
| 54 | | | 3 | 2 |
| 55 | | | 3 | 2 |
| 56 | | | 3 | 2 |
| 57 | | | 3 | 2 |
| 58 | | | 3 | 2 |
| 59 | | | 3 | 2 |
| 60 | | | 3 | 2 |

The data in Table 7 evidence the efficacy of a Composition D for repellency of the American dog tick.

EXAMPLE 8

In this example, Composition D was evaluated versus untreated human skin, against the American dog tick. The test arena was 4 cm in diameter (12.56 cm$^2$) on the right inner thigh of the human male subject, just proximal to the kneecap.

100 μL of Composition D were applied to the left half of the arena. Ticks, unfed males/females of the American dog tick, *Dermacenter variabilis*, were added to the arena 30 seconds after treatment with Composition D. As a control, the right and left halves of the arena were not treated. The test apparatus was a petri plate top with the opening covered with aluminum screening. The assay was conducted in light at room temperature. The control assay was conducted first. The data are set out in Table 8 below, with times in minutes after application of ticks.

TABLE 8

| Time | Control | | Composition D | |
|---|---|---|---|---|
| | L | R | Treated (L) | Untreated (R) |
| First group of 5 ticks | | | | |
| 0 min | | | 5 | 0 |
| 1 | 0 | 5 | 1 | 4 |
| 2 | 0 | 5 | 3 | 2 |
| 3 | 1 | 4 | 1 | 4 |
| 4 | 2 | 3 | 0 | 5 |
| 5 | 1 | 4 | 0 | 5 |
| 6 | 1 | 4 | 1 | 4 |
| 7 | 1 | 4 | | |
| 8 | 2 | 3 | 2 | 3 |
| 9 | 4 | 1 | 1 | 4 |
| 10 | 4 | 1 | | |
| 11 | 4 | 1 | 1 | 4 |
| 12 | 3 | 2 | | |
| 13 | 3 | 2 | | |
| 14 | 3 | 2 | | |
| 15 | 5 | 0 | | |
| 16 | 4 | 1 | | |
| 17 | 4 | 1 | | |
| 18 | 4 | 1 | | |
| 19 | 5 | 0 | | |
| 20 | 5 | 0 | | |
| Second group of 5 ticks | | | | |
| 30 | | | 6 | 0 |
| 31 | | | 3 | 3 |
| 32 | | | 1 | 5 |
| 33 | | | 2 | 4 |
| 34 | | | 3 | 3 |
| 35 | | | 3 | 3 |

EXAMPLE 9

In this example, Composition D was evaluated versus untreated human skin, against the American dog tick. The test arena was 4 cm in diameter (12.56 cm$^2$) on the left inner thigh of the human male subject, just proximal to the kneecap. 100 μL of Composition D were applied to the left half of the arena. Ticks, unfed males/females of the American dog tick, *Dermacenter variabilis*, were added to the arena in less than two minutes after treatment with Composition D. As a control, the right and left halves of the arena were not treated. The test apparatus was a petri plate top with the opening covered with aluminum screening. The assay was conducted in light at room temperature. The control assay was conducted first. The data are set out in Table 9 below, with times in minutes after application of ticks.

TABLE 9

| | Control | | Composition D | |
|---|---|---|---|---|
| Time | L | R | Time | Treated (L) | Untreated (R) |
| First tick | | | | | |
| 0 min | 1 | 0 | 0 | 0 | 1 |
| 1 | 0 | 1 | 1 | 0 | 1 |
| 2 | 1 | 0 | 2 | 1 | 0 |
| 3 | 0 | 1 | 3 | 0 | 1 |
| 4 | 0 | 1 | 4 | 0 | 1 |
| 5 | 0 | 1 | 5 | 0 | 1 |
| Second tick | | | | | |
| 0 min | 0 | 1 | 5 (0) | 1 | 0 |
| 1 | 1 | 0 | 6 (1) | 1 | 0 |
| 2 | 1 | 0 | 7 (2) | 0 | 1 |
| 3 | 1 | 0 | 8 (3) | 1 | 0 |
| 4 | 1 | 0 | 9 (4) | 0 | 1 |
| 5 | 0 | 1 | 10 (5) | 0 | 1 |
| Third tick | | | | | |
| 0 min | 0 | 1 | Experiment stopped | | |
| 1 | 1 | 0 | | | |
| 2 | 1 | 0 | | | |
| 3 | 1 | 0 | | | |
| 4 | 1 | 0 | | | |
| 5 | 1 | 0 | | | |

When the experiment was stopped, the screen was removed from the apparatus holding the third tick and the apparatus was applied to the treated/untreated area without the screen in place (tick in direct contact with human subject's skin). Ticks during a period of 1-2 minutes, walked into and out of the treated area. As a further check on the tick activity, the area which had been treated with Composition D was sprayed with a 25% commercial DEET repellent until runoff, and the apparatus was reapplied without the screen (with the same tick used in the third tick test). The tick again walked into and out of the treated area for 1-2 minutes.

EXAMPLE 10

In this example, Composition D was evaluated versus untreated human skin, against the American dog tick. The test arena was 4 cm in diameter (12.56 cm$^2$) on the left inner thigh of the human male subject, just proximal to the kneecap. 100 μL of Composition D were applied to the left half of the arena. Ticks, unfed males/females of the American dog tick, *Dermacenter variabilis*, were added to the arena in less than two minutes after treatment with Composition D. As a control, the right and left halves of the arena were not treated. The test apparatus was a petri plate top with the opening covered with aluminum screening. The assay was conducted in darkness at room temperature. The control assay was conducted first. The data are set out in Table 10 below, with times in minutes after application of ticks.

TABLE 10

| Time | Control | | Composition D | |
|---|---|---|---|---|
| | L | R | Treated (L) | Untreated (R) |
| First group of 5 ticks | | | | |
| 0 min | | | 4 | 1 |
| 5 | 5 | 0 | | |
| 10 | 2 | 3 | | |
| 15 | 4 | 1 | 1*** | 4 |
| 20 | 3 | 2 | | |
| 25 | 2 | 3 | | |

TABLE 10-continued

|  | Control | | Composition D | |
|---|---|---|---|---|
| Time | L | R | Treated (L) | Untreated (R) |
| 30 | 3 | 2 | 1 | 4 |
| 45 | 2 | 3 | 0 | 5 |
| 60 | 1 | 4 | 1 | 4 |
| Second group of 5 ticks | | | | |
| 60 (0) | | | 4 | 1 |
| 1 h: 15 min (15) | | | 2 | 3 |
| 1: 30 (30) | | | 3 | 2 |
| 1: 45 (45) | | | 2 | 3 |
| 2: 00 (60) | | | 1 | 4 |

EXAMPLE 11

In this example, Composition D was evaluated versus untreated human skin, against the American dog tick. The test arena was 4 cm in diameter (12.56 cm$^2$) on the right inner thigh of the human male subject, just proximal to the kneecap. 100 μL of Composition D were applied to the left half of the arena. Ticks, unfed males/females of the American dog tick, *Dermacenter variabilis*, were added to the arena in less than two minutes after treatment with Composition D. As a control, the right and left halves of the arena were not treated. The test apparatus was a petri plate top with the opening covered with aluminum screening. The assay was conducted in darkness at room temperature. The control assay was conducted first. The data are set out in Table 11 below, with times in minutes after application of ticks.

TABLE 11

|  |  | Control | | Composition D | |
|---|---|---|---|---|---|
| Time | Rep | L | R | Treated (L) | Untreated (R) |
| 0 min | 1 | | | 4 | 1 |
|  | 2 | | | 5 | 0 |
| 10 | 1 | 4 | 1 | 2 | 3 |
|  | 2 | 2 | 3 | 2 | 3 |
| 20 | 1 | 2 | 3 | 1 | 4 |
|  | 2 | 3 | 2 | 1 | 4 |
| 30 | 1 | 3 | 2 | 1 | 4 |
|  | 2 | 0 | 5 | 3 | 2 |
| 40 | 1 | 3 | 2 | 1 | 4 |
|  | 2 | 3 | 2 | 1 | 4 |
| 50 | 1 | 2 | 3 | 3 | 2 |
|  | 2 | 3 | 2 | 1 | 4 |
| 60 | 1 | 3 | 2 | 3 | 2 |
|  | 2 | 3 | 2 | 2 | 3 |

EXAMPLE 12

In this example, the test arena was a 10 cm diameter plastic petri plate (78.5 cm$^2$ bottom surface area). The inside bottom of the plate was covered with two half circles of white copy paper, separated by a 3 mm void at the centerline. Composition D was applied to the left half of the arena in the amount of 537 μL. Ticks, unfed males/females of the American dog tick, *Dermacenter variabilis*, were added to the arena less than two minutes after application of composition D. The assay was conducted in darkness at room temperature. The data are set forth in Table 12 below, with times given in minutes after application of ticks. It was not determined whether ticks were still alive at the 9 hours 43 minutes reading.

TABLE 12

|  | Composition D | |
|---|---|---|
| Time | Treated (L) | Untreated (R) |
| 30 min | 1 | 4 |
| 45 | 0 | 5 |
| 60 | 0 | 5 |
| 1 h: 30 min | 0 | 5 |
| 9 h: 43 min | 0 | 5 |

EXAMPLE 13

In this example, the test arena was 4 cm in diameter (12.56 cm$^2$) on the left inner thigh of the human male subject, just proximal to the kneecap. As a control, the left and right halves of the arena were untreated. A 7% DEET composition was applied to the left half of the arena in the amount of 100 μL. Ticks, unfed males/females of the American dog tick, *Dermacenter variabilis*, were added to the arena 1 minute 45 seconds after application of the 7% DEET composition. The assay was conducted in darkness at room temperature. The test apparatus was a petri plate top with the opening covered with aluminum screening. The base for the 7% DEET composition was mostly alcohol; it was not apparent, whether the one minute 45 second waiting period was sufficient for all of the alcohol to evaporate from the skin. The data are set forth in Table 13 below, with times given in minutes after application of ticks.

TABLE 13

|  | Control | | 7% DEET Composition | |
|---|---|---|---|---|
| Time | L | R | Treated (L) | Untreated (R) |
| 0 min | 2 | 3 | 5 | 0 |
| 5 | 2 | 3 | 5 | 0 |
| 10 | 3 | 2 | 5 | 0 |
| 15 | 2 | 3 | 4 | 1 |
| 20 | 1 | 4 | 4 | 1 |
| 25 | 1 | 4 | 4 | 1 |
| 30 | 0 | 5 | 4 | 1*** |
| 35 | 3 | 2 | | |
| 40 | 2 | 3 | | |
| 45 | 3 | 2 | | |
| 50 | 3 | 2 | | |
| 55 | 3 | 2 | | |
| 60 | 3 | 2 | | |

***Only one tick moved since the beginning of the experiment, such movement occuring between 10 and 15 minutes. The experiment was stopped at 30 minutes, and that this time, all ticks appeared to be alive, i.e., they moved when touched with a blunt probe.

EXAMPLE 14

In this example, the test arena was a 10 cm diameter plastic petri plate (78.5 cm$^2$ bottom surface area). The inside bottom was covered with two half circles of white copy paper separated by a 3 mm void at the centerline. As a control, the left and right halves of the arena were untreated. A 7% DEET composition was applied to the left half of the arena in the amount of 537 μL. Ticks, unfed males/females of the American dog tick, *Dermacenter variabilis*, were added to the arena after the 7% DEET composition was no longer visible. The assay was conducted in darkness at room temperature. The data are set forth in Table 14 below, with times given in minutes after application of ticks.

TABLE 14

| | 7% DEET Composition | |
|---|---|---|
| Time | Treated (L) | Untreated (R) |
| 1 min | 2 | 3 |
| 10 | 1 | 4 |
| 20 | 1 | 4 |
| 30 | 1 | 4 |
| 40 | 2 | 3 |
| 50 | 2 | 3 |
| 60 | 1 | 4 |
| 1 h:10 min | 1 | 4 |
| 1:20 | 1 | 4 |
| 2:00 | 2 | 3 |
| 3:30 | 2 | 3 |
| 4:30 | 2 | 3*** |

***All ticks moved when touched with a blunt probe at four hours, 30 minutes.

EXAMPLE 15

The objective of this experiment was to evaluate mosquito repellency of compositions of the present invention under natural field conditions.

All tests were conducted with wild populations on a nature trail at Howell Woods Environmental Education Center, Bentonville, N.C. Two specific study locations were selected: a three meter wide trail through a heavily wooded area, (forest) and on a 1.2 m wide plank bridge, approximately 0.6 m above the surface of a heavily wooded pond.

Two repellent compositions were tested: a 2.4% soybean emulsion formulated with a sunscreen formulation having an SPF 20 factor (Composition F); and a 4% soybean methyl ester emulsion formulated with 8% undecanone (Composition G).

The experimental protocol was based on the EPA Product Performance Test Guidelines OPPTS 810.3700 Insect Repellents for Human Skin and Outdoor Premises and PMRA requirements (Canada). For this experiment, the test area was the surface of the arm just distal to the elbow to the most distal end of the hand. The following test applications were used: (a) control (no treatment); (b) 2.0 mL of Composition F; and (c) 1.5 mL of Composition G. Composition F was a viscous cream. The application of the repellent to all subjects was conducted within a 10 minute time period. Landing counts in the field were conducted at 2, 3, 4 and 4.5 hours after application of the repellent, with the 4.5 hour assay conducted at dusk. The repellent volume to be applied was measured with a P5000 Gilson Pippetmann, and applied directly to the subject's skin. The applied repellent was spread with a free hand to cover the entire area to be treated. Subjects were requested to remain in the reception area until about one hour prior to the first field test (the two-hour post-treatment test). Each replicate was one person (control, one male and one female; Composition F (2 mL), two males and one female; Composition G (1.5 mL), two males and one female), and the same person was tested at each time (total number of human subjects=eight). At approximately 1 hour before the field test, all subjects traveled by car for about 40 minutes to the parking lot of the visitor center at Howell Woods.

All subjects were dressed in their personal clothing of choice, with only the treated or control area of their forearm, their hands, and their head exposed. Each subject were at least two shirts. The head of each subject was covered with hat and mosquito net, and the hand on the subject's untreated arm was covered with a latex disposable glove. The only exposed skin for mosquito landings was the control or treated surface of the forearm and hand of one arm. The pants for both legs was either taped tight against the ankles or inserted into the subjects' socks. Each subject was provided with a pencil and data form to record landing counts, and all test subjects then walked together about 0.25 mile to the test location.

Two distinctly different test locations, forest and bridge, were used, as previously described. Each test location covered a linear area of the 37 m. Two to three test measurements were made at a different site in the same test location (forest or bridge). At each time (2-4.5 hours post-treatment of the repellent). Changes in the site within a location were achieved by asking subjects to randomly exchange positions with other subjects. After each test time (2, 3 and 4 hours), the subjects all returned together to the parking lot of the Howell Woods Visitor's Center. Between the four and 4.5 hours reading, the subjects remained in the forest location. Subjects were asked to count the number of mosquito landings over a given observation, which was initiated and ended by voice communication from one of the control subjects. Landings were defined as a mosquito on the subject's forearm or hand for at least two seconds and/or after observing probing. The subjects were asked to physically remove the mosquito from their arm with their free hand using at least a brushing motion to prevent mosquito bites. The estimated skin surface area for the control and treatments was 900 cm² each. All landing count measurements were taken simultaneously across reps at each location, and at different sites within a location.

Results are set out below in Table 15.

TABLE 15

Mosquito landing counts on the surface of arm from just distal to the elbow to the most distal end of hand.[a]

| | | Control | | Composition F | | | Composition G | | |
|---|---|---|---|---|---|---|---|---|---|
| Parameter | | | | | | | | | |
| Time | Location | Rep 1 | Rep 2 | Rep 1 | Rep 2 | Rep 3 | Rep 1 | Rep 2 | Rep 3 |
| 2 hrs | Forest | 4.60/min | 2.40 | 0 | 0 | 0 | 0 | 0 | 0 |
| 2 hrs | Bridge | 8.40 | 19.20 | 0 | 0 | 0 | 0 | 0 | 0.33[b] |
| 2 hrs | Bridge | 9.67 | 16.67 | 0 | 0 | 0 | 0 | 0 | 0 |
| 3 hrs | Forest | 7.33 | 9.00 | 0.33[b] | 0 | 0.33 | 0 | 0 | 0 |
| 3 hrs | Bridge | 12.67 | 22.00 | 0 | 0 | 1.00 | 0 | 0 | 0 |
| 3 hrs | Bridge | 11.33 | 16.00 | 0 | 0 | 0.67 | 0.33 | 0 | 0 |
| 4 hrs | Forest | 13.00 | 15.00 | 0 | 1.00 | 1.33 | 0.33 | 0 | 0.33 |
| 4 hrs | Bridge | 5.33 | 11.00 | 0 | 0 | 2.33 | 0 | 0 | 1.33 |
| 4 hrs | Bridge | 17.33 | 15.00 | 0 | 0 | 0.67 | 0.67 | 0 | 1.00 |

TABLE 15-continued

Mosquito landing counts on the surface of arm from just distal to the elbow to the most distal end of hand.[a]

| Parameter | | Control | | Composition F | | | Composition G | | |
|---|---|---|---|---|---|---|---|---|---|
| Time | Location | Rep 1 | Rep 2 | Rep 1 | Rep 2 | Rep 3 | Rep 1 | Rep 2 | Rep 3 |
| 4.5 hrs | Bridge | 14.33 | 21.00 | 0 | 0 | 0.33 | 0 | 0 | 0.33 |
| 4.5 hrs | Forest | 18.67 | 7.67 | 0 | 1.33 | 0.33 | 0.33 | 0 | 0.33 |

[a]Time = elapsed time after application of repellent.
[b]Mosquito landing on fingernail.

The percent repellency based on the Table 15 results is set out in Table 16 below.

TABLE 16

Percent repellency on the surface of arm from just distal to the elbow to the most distal end of hand.[a]

| Parameter | | Control mean | Composition F | | | Composition G | | |
|---|---|---|---|---|---|---|---|---|
| Time | Location | landings/min | Rep 1 | Rep 2 | Rep 3 | Rep 1 | Rep 2 | Rep 3 |
| 2 hrs | Forest | 3.50 | 100 | 100 | 100 | 100 | 100 | 100 |
| 2 hrs | Bridge | 13.80 | 100 | 100 | 100 | 100 | 100 | 97.61[b] |
| 2 hrs | Bridge | 13.17 | 100 | 100 | 100 | 100 | 100 | 100 |
| 3 hrs | Forest | 16.33 | 97.98[b] | 100 | 97.98 | 100 | 100 | 100 |
| 3 hrs | Bridge | 17.34 | 100 | 100 | 94.23 | 100 | 100 | 100 |
| 3 hrs | Bridge | 13.66 | 100 | 100 | 95.10 | 97.58 | 100 | 100 |
| 4 hrs | Forest | 14.00 | 100 | 92.86 | 90.50 | 97.64 | 100 | 97.64 |
| 4 hrs | Bridge | 8.16 | 100 | 100 | 71.45 | 100 | 100 | 83.70 |
| 4 hrs | Bridge | 16.16 | 100 | 100 | 95.85 | 95.85 | 100 | 93.81 |
| 4.5 hrs | Bridge | 17.66 | 100 | 100 | 98.13 | 100 | 100 | 98.13 |
| 4.5 hrs | Forest | 13.17 | 100 | 89.90 | 97.49 | 97.49 | 100 | 97.49 |

[a]Time = elapsed time after application of repellent.
[b]Mosquito landing on fingernail.

In generating the data of Table 15 and Table 16, the assay time for the Rep 1 control was typically three minutes, but some of the earlier measurements were made at five minutes. Due to the high landing counts for the Rep 2 control at two hours, this subject was provided an option to stop their counts at one minute. The assay time for the treated subjects was the same as for the Rep 1 control. Table 15 shows the landing counts per minute, for the controls and treatments. Accept for the two-hour Forest assay for Reps 1 and 2 and one of the bridge measurements for Rep 1 at four hours, the landing counts exceeded seven per minute, which was greater than the minimum activity level acceptable for conducting data analyses.

Table 16 shows the mean control landings per minute for each test. And percent repellency for each Rep at each location and site within a location for each of the compositions F and G. Percent repellency for each Rep was calculated based on its control as follows: [(mean landing counts per minute for control)−(landing counts per minute for Rep)/mean landing counts per minute for control]×100%. The repellency data shown in Table 16 evidence high effectiveness of both Compositions F and G. The study was concluded at 4.5 hours because of lack of natural light, as needed to observe mosquito landings.

Mosquitoes were collected from the subjects at the end of the assays. The mosquitoes collected were identified as follows: 12 *Ochlerotatus anlanticus/tormentus*, 4 *Pshrophora ferox* and 1 *Psorophora columbiae*.

While the invention has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A pest-combating composition suitable for topical application to human skin as an insect repellant, comprising at least 2.4% of soy methyl ester and at least 8% of undecanone and wherein said percentages are based on the total weight of the composition, and wherein said composition further comprises at least one of coconut oil, glycerin, and citric acid.

2. The composition of claim 1, wherein the soy methyl ester is in an emulsified form.

3. The composition of claim 1, wherein the soy methyl ester comprises a mixture of $C_{16}$-$C_{18}$ saturated and $C_{18}$ unsaturated methyl esters.

4. A DEET-free composition according to claim 1.

5. The composition of claim 1, comprising said soy methyl ester in an emulsified form, and at least one additional ingredient selected from the group consisting of fillers, dispersants, water, non-aqueous solvent media, surfactants, suspension agents, sticking agents, stabilizers, preservatives, dyes, pigments, masking agents, emollients, excipients, and post-application detection agents.

6. The composition of claim 1, comprising at least one additional ingredient selected from the group consisting of fillers, dispersants, surfactants, suspension agents, sticking agents, stabilizers, preservatives, dyes, pigments, masking agents, emollients, excipients, and post-application detection agents.

7. The composition of claim 1, further comprising coconut oil.

8. The composition of claim 1, further comprising glycerin.

9. The composition of claim 1, further comprising citric acid.

10. The composition of claim 1, formulated as a spray composition.

11. The composition of claim 1, further comprising a sticking agent.

12. The composition of claim 1, formulated as a spray composition, said composition including from about 2 to about 15% by weight of soy methyl ester, and from about 8 to about 30% by weight of undecanone, wherein said weights are based on total weight of the composition, said composition further including at least one of water, coconut oil, glycerin, geranium oil, citric acid, lecithin, sodium bicarbonate and vanilla.

13. The composition of claim 12, comprising 2% by weight of soy methyl ester, based on total weight of the composition, said composition including purified water, coconut oil, glycerin, geranium oil, castor oil, lecithin and vanilla.

14. The composition of claim 1, wherein the soy methyl ester has a concentration of from about 2.4% to about 15% of by weight, based on total weight of the composition.

15. The composition of claim 1, wherein the soy methyl ester has a concentration of from about three to about 10% by weight, based on total weight of the composition.

16. The composition of claim 10, comprising 2.4%-15% by weight of soy methyl ester, based on total weight of the composition, said composition including purified water, coconut oil, glycerin, geranium oil, citric acid, lecithin, sodium bicarbonate and vanilla.

17. A pest-combating composition suitable for topical application to human skin as an insect repellant, comprising a soy methyl ester (SME) emulsion, and undecanone, wherein concentration of soy methyl ester in said composition is in a range of from 2.4% to 8% by weight, based on total weight of the composition and the concentration of undecanone in said composition is at least 8% by weight based on the total weight of said composition.

18. The pest-combating composition of claim 17, wherein undecanone is present in said composition at concentration up to 30% by weight, based on the total weight of the composition.

19. The pest-combating composition of claim 17, further comprising glycerin.

* * * * *